United States Patent [19]

Davies

[11] 4,370,313

[45] Jan. 25, 1983

[54] NITROFURANTOIN DOSAGE FORM

[75] Inventor: William L. Davies, Norwich, N.Y.

[73] Assignee: Eaton Laboratories, Inc., Manati, P.R.

[21] Appl. No.: 314,656

[22] Filed: Oct. 26, 1981

[51] Int. Cl.³ .................. A61K 9/32; A61K 31/345
[52] U.S. Cl. ................................................. 424/32
[58] Field of Search ............................ 424/19-22, 424/32-33

[56] References Cited

U.S. PATENT DOCUMENTS

| | | | |
|---|---|---|---|
| 3,577,512 | 5/1971 | Shepherd et al. | 424/32 |
| 3,641,237 | 2/1972 | Gould et al. | 424/32 |
| 3,775,537 | 11/1973 | Lehmann | 424/21 |
| 3,926,188 | 12/1975 | Baker et al. | 424/19 |
| 3,954,959 | 5/1976 | Pedersen | 424/21 |
| 4,060,598 | 11/1977 | Groppenbacher et al. | 424/32 |
| 4,083,949 | 4/1978 | Benedikt | 424/19 |
| 4,122,157 | 10/1978 | Huber | 424/21 |
| 4,177,256 | 12/1979 | Michaels et al. | 424/19 |
| 4,193,985 | 3/1980 | Bechgaard et al. | 424/32 |
| 4,289,795 | 9/1981 | Bogentoft et al. | 424/21 |

OTHER PUBLICATIONS

R. Groning, Int. J. Pharm. 8(3): 175–181, May 1981, "Control of Release and Bioavailability of Drugs-Investigations into Renal Elimination of Nitrofurantoin".

Primary Examiner—Shep K. Rose
Attorney, Agent, or Firm—Anthony J. Franze

[57] ABSTRACT

A nitrofurantoin dosage form comprising a nitrofurantoin salt and excipients therefor enterically coated with an acrylic resin is described.

3 Claims, No Drawings

NITROFURANTOIN DOSAGE FORM

This invention is concerned with the treatment of urinary track infections and the use of nitrofurantoin therein.

Nitrofurantoin has been used successfully for many years for the treatment of urinary tract infections. Its presumed mode of action is based upon its interference with several bacterial enzyme systems. Bacteria develop only a limited resistance to nitrofurantoin clinically. Nitrofurantoin is indicated for the treatment of urinary tract infections due to susceptible strains of *E. coli, enterococci, S. aureus* and certain susceptible strains of Klebsiella species, Enterobacter species and Proteus species.

The use of nitrofurantoin in the traditional pharmaceutical dosage forms such as powders, tablets, capsules, suspensions and solutions has required the peroral administration of usually four unit doses per day. Many patients using nitrofurantoin are elderly and often taking several other daily medications for other therapy. Accordingly, it is important for the convenience of the patient, and more essentially to ensure patient compliance to a particular therapeutic regimen, that the number of unit doses of medication administered perorally per day be minimized.

In an effort to overcome these patient inconvenience and compliance problems, attempts have been made by numerous researchers to design conventional, classical sustained/prolonged release dosage formulations of nitrofurantoin for purposes of reducing the number of daily perorol dose administrations by the patient. All attempted dosage form designs have failed to significantly prolong urine levels of nitrofurantoin beyond those achieved with the formulations presently available. Nitrofurantoin appears to be a poor candidate for the classical sustained/prolonged release pharmaceutical product. This is attributable to the preferred absorption of nitrofurantoin in a limited segment of the human gastrointestinal tract, i.e., the duodenum. While the majority of attempts to deliver a sustained/prolonged release nitrofurantoin dosage form have been successful from the standpoint that they slow the release of the active drug substance from the dosage form on peroral ingestion (as evidenced by reduced human bioavailability of the drug substance) there has been no evidence of a delayed urinary excretion pattern of nitrofurantoin beyond that achieved with available dosage forms. There is available no formulation to afford a patient a twice daily dosing regimen for the control of urinary tract infections with nitrofurantoin.

In accordance with the present invention of a nitrofurantoin dosage form, a twice a day dosing regimen is achieved where available traditional product formulations require a three to four times a day dosing schedule. This formulation is not a dosage form of continuous therapy typical of sustained/prolonged release preparations but rather this design represents intermittent dosing by the administration of a single oral dosage form. This dosage form is not designed for steady state therapy; the usual "peak and valley" type of blood/urine profiles associated with intermittent dosing therapy may be evident. The advantages of the instant dosage form are patient convenience and compliance due to a reduced daily peroral dosing regimen.

The instant invention provides a nitrofurantoin dosage form which utilizes an enteric coated, rapidly disintegrating/dissolving tablet consisting of a readily soluble salt of nitrofurantoin. Such a dosage form provides a convenient method of twice a day patient dosing in conjunction with conventional dosage forms of nitrofurantoin.

In order to achieve the desired twice a day dosing regimen with orally administered nitrofurantoin, the drug from the enteric coated dosage form must be released and available for absorption in the gastrointestinal tract approximately 3 to 4 hours after peroral ingestion. An initial dose of nitrofurantoin from conventional dosage forms is immediately released and available for absorption. With typical human gastric emptying times in the order of ½ to 2 hours, the immediately available dose of nitrofurantoin is at its primary absorption site in the gastrointestinal tract, i.e., the duodenum, in 1 to 2 hours. With its very rapid elimination rate from the blood, e.g., less than 1 hour, nitrofurantoin urinary level peaks are expected in about 2 to 3 hours.

The following examples describe the preparation of the enteric coated dosage form of nitrofurantoin of this invention.

EXAMPLE I

| Per Tablet | Tablet Composition | Percentage |
|---|---|---|
| 238 mg* | Nitrofurantoin sodium hydrate | 48.8 |
| 175 mg | Microcrystalline cellulose | 35.9 |
| 25 mg | Sodium starch glycollate | 5.1 |
| 25 mg | Corn starch | 5.1 |
| 20 mg | Talc | 4.1 |
| 5 mg | Magnesium stearate | 1.0 |

*Equivalent to 200 mg nitrofurantoin.

The ingredients of Example I are mixed according to acceptable pharmaceutical manufacturing practices. The finished blend is screened and 488 mg convex core tablets compressed by direct compression using a suitable tablet press yielding tablets approximately 11 mm in diameter and 5.4 mm in height.

In Example I the active drug substance may take the form of a salt (sodium or potassium) of nitrofurantoin or one of its solvates, e.g., hydrate. Excipients (pharmaceutical adjuvants) may include (1) fillers to add bulk and improve compressibility, e.g., lactose, starch, sugar-alcohols, cellulose derivatives, calcium sulfate or phosphate, (2) disintegrants to disintegrate the dosage form, e.g., starch, sodium starch glycollate, cellulose derivatives, alginates, gums, effervescent mixtures, (3) binders to form granules or improve compressibility, e.g., gums, sugars, starch, cellulose derivatives, alginates, polyvinylpyrrolidone, (4) lubricants to reduce friction, e.g., stearic acid, metallic stearates, high melting point waxes, talc, (5) agents to improve dissolution, e.g., surfactants, alkaline buffers and (6) glidants to improve flow, e.g., starch, talc, silicate.

EXAMPLE II

| Composition | Percentage |
|---|---|
| Eudragit-S 12.5% Isopropanol Suspension | 45.7 |
| Polyethylene glycol 6000 33% Aqueous Solution | 3.5 |
| Talc | 2.5 |
| Isopropanol/Acetone 1:1 | 48.3 |

Eudragit-S (Röhm Pharma, Darmstadt, West Germany) is an anionic polymer synthesized from methacrylic acid and methacrylic acid methyl ester.

In Example II the concentration of excipients and solvents in the film forming solution may be varied to affect drying rates with various processing temperatures and equipment. Alternate solvents such as methanol, ethanol, or methylene chloride as well as other plasticizers such as castor oil, glycerine, propylene glycol or phthalate derivatives and enteric film formers such as shellac, cellulose acetate phthalate, hydroxypropyl methyl cellulose may be employed.

Compressed tablets from Example I are enteric coated by spraying the Eudragit-S suspension from Example II onto their surfaces as tablets rotate in a conventional coating pan. Coating thickness required to produce an even, uninterrupted surface distribution varies between 4.0 and 7.2 mg/cm$^2$ a lacquer dry substance. Coat thickness may vary beyond this range depending upon production scale and process equipment. Air suspension coating techniques are also applicable.

To exemplify the effectiveness of the Eudragit-S enteric film coat in delaying absorption and prolonging urinary excretion of nitrofurantoin in humans an 18 subject crossover design bioavailability study was performed comparing the test dosage forms against a commercially marketed nitrofurantoin control preparation at equivalent 200 mg doses.

Dosage forms were administered to healthy, non-fasted human subjects who voided every 2 hours for 14 hours and again at 24 hours. Nitrofurantoin levels in the urine were measured by spectrophotometry. Results are depicted in Table I.

TABLE I
Percent Nitrofurantoin Urinary Recovery Following Oral Administration of Eudragit-S Enteric Coated Sodum Nitrofurantoin Tablets and a Commercial Marketed Product Control

| Urine Recovery Inverval | Eudragit-S Enteric Film Surface Coat Thickness | | Macrocrystalline Nitrofurantoin Capsule Control |
|---|---|---|---|
| | 4.0 mg/cm$^2$ | 5.6 mg/cm$^2$ | |
| 0-2 hr | 0% | 0% | 4.6% |
| 2-4 hr | 7.5% | 1.5% | 9.7% |
| 4-6 hr | 12.0% | 7.7% | 6.2% |
| 6-8 hr | 1.7% | 5.8% | 1.2% |
| 8-10 hr | 0.5% | 1.4% | 0.3% |
| 10-12 hr | 1.4% | 0.4% | 0% |
| 12-14 hr | 0.7% | 0.1% | 0% |
| 14-24 hr | 0.5% | 0% | 0% |
| Total | 24.3% | 16.9% | 22.0% |

Bioavailability results as shown in Table I demonstrate the ability of Eudragit-S enteric film to delay release and absorption and hence urinary excretion of nitrofurantoin relative to a non-enteric coated control preparation. Zero recovery in the 0-2 hour collection interval for the enteric coated tablet dosage form indicates delayed gastrointestinal tract absorption. Peak urine levels in the 4-6 hour interval for the enteric coated tablet dosage forms is further evidence that delayed absorption in imparted by the Eudragit-S film component. Urine recovery of nitrofurantoin from the control is evident in the 0-2 hour collection interval and nitrofurantoin urine levels peak earlier at 2-4 hours.

Delayed gastrointestinal absorption and urinary excretion with Eudragit-S enteric coating is affected by tablet surface film thickness. With an enteric film thickness increase from 4.0 mg/cm$^2$ to 5.6 mg/cm$^2$, nitrofurantoin urine excretion shifts from the majority in 2-6 hours to the majority of nitrofurantoin excreted in 4-8 hours.

The administration of the dosage form of Examples I and II concomitantly or in conjunction with conventional pharmaceutical dosage forms of nitrofurantoin enables a reduced dosage regimen, the conventional forms supplying immediate availability of nitrofurantoin and the enteric coated form a delayed availability.

The administration conjunctively of these two forms can be accomplished in a number of ways. Preferably, this is achieved by spray coating a composition comprising from 25-50 mg of nitrofurantoin onto the enteric coated dosage form of Examples I and II. Alternatively, in addition to such coated tablet form, the dosage form may consist of a packet or a capsule containing pH sensitive enteric coated nitrofurantoin sodium granules or tablets (for the delayed dose) and uncoated or simply film-coated nitrofurantoin powder, granules or tablets (for the immediate dose), or the dosage form may consist of a wet granulation, dry granulation or direct compression layered tablet or a tablet within a tablet or capsule. Each dosage form contains the immediate release dose and the delayed dose (through pH sensitive enteric coating) as described above.

What is claimed is:

1. A nitrofurantoin dosage form as a tablet containing a salt of nitrofurantoin or a hydrate thereof and excipients therefor enterically coated with an acrylic resin of the class consisting of an anionic polymer synthesized from methacrylic acid and methacrylic acid methyl ester.

2. A nitrofurantoin dosage form as a tablet consisting of:

| | |
|---|---|
| 238 mg | Nitrofurantoin sodium hydrate |
| 175 mg | Microcrystalline cellulose |
| 25 mg | Sodium starch glycollate |
| 25 mg | Corn starch |
| 20 mg | Talc |
| 5 mg | Magnesium stearate | enterically coated with a composition consisting of:

| | Percentage |
|---|---|
| Anionic polymer synthesized from methacrylic acid and methacrylic acid methyl ester 12.5% Isopropanol Suspension | 45.7 |
| Polywax 6000 33% Aqueous Solution | 3.5 |
| Talc | 2.5 |
| Isopropanol/Acetone 1:1 | 48.3 |

3. A nitrofurantoin dosage form comprising a salt of nitrofurantoin or a hydrate thereof and excipients therefor enterically coated with an acrylic resin of the class consisting of an anionic polymer synthesized from methacrylic acid and methacrylic acid methyl ester.

* * * * *